(12) United States Patent
Goodfield et al.

(10) Patent No.: US 10,490,034 B2
(45) Date of Patent: Nov. 26, 2019

(54) STATUS OR ALARM INDICATOR DEVICE

(71) Applicant: Huntleigh Technology Limited, Dunstable (GB)

(72) Inventors: Clive Goodfield, Llantrisant (GB); Julie Acosta, Fair Oaks Ranch, TX (US); Bruce McNeil, San Antonio, TX (US)

(73) Assignee: Huntleigh Technology Limited (GB)

( * ) Notice: Subject to any disclaimer, the term of this patent is extended or adjusted under 35 U.S.C. 154(b) by 0 days.

(21) Appl. No.: 15/664,328

(22) Filed: Jul. 31, 2017

(65) Prior Publication Data

US 2017/0330430 A1    Nov. 16, 2017

Related U.S. Application Data

(63) Continuation-in-part of application No. PCT/US2016/015860, filed on Jan. 30, 2016.

(60) Provisional application No. 62/110,229, filed on Jan. 30, 2015.

(51) Int. Cl.
| | |
|---|---|
| *G08B 5/36* | (2006.01) |
| *A61G 7/05* | (2006.01) |
| *A61H 9/00* | (2006.01) |
| *A61B 5/022* | (2006.01) |
| *F21V 33/00* | (2006.01) |

(52) U.S. Cl.
CPC ............... *G08B 5/36* (2013.01); *A61G 7/05* (2013.01); *A61H 9/0078* (2013.01); *A61B 5/022* (2013.01); *A61B 2560/0406* (2013.01); *A61H 2201/50* (2013.01); *A61H 2209/00* (2013.01); *F21V 33/0068* (2013.01)

(58) Field of Classification Search
None
See application file for complete search history.

(56) References Cited

U.S. PATENT DOCUMENTS

| | | | | |
|---|---|---|---|---|
| 5,497,968 A | * | 3/1996 | Hewko | A61G 1/04 248/214 |
| 5,611,096 A | * | 3/1997 | Bartlett | A61G 7/001 5/424 |
| 5,935,152 A | * | 8/1999 | Merry | A61N 1/39 607/5 |
| 5,959,287 A | | 9/1999 | Myers et al. | |
| 6,247,674 B1 | * | 6/2001 | Jawidzik | F16M 13/005 248/213.2 |

(Continued)

FOREIGN PATENT DOCUMENTS

EP    2090261 A1    8/2009

*Primary Examiner* — Curtis J King
(74) *Attorney, Agent, or Firm* — The Webb Law Firm (57) ABSTRACT

An indicator device includes a casing having rearward projecting elements from which coupling hooks extend. The device includes a downwardly facing window as well as two forwardly or upwardly extending windows. The device includes lights or lamps disposed adjacent the windows for generating status and/or warning signals. The device can be hooked onto a support such as a footboard of a hospital bed or placed on a floor with a window exposed. The window is able to direct light from the lighting elements to a surface such as a floor or footboard or other surface. This assists in a caregiver seeing light emanating from the device even when this is covered.

14 Claims, 4 Drawing Sheets

(56) References Cited

U.S. PATENT DOCUMENTS

| | | | | |
|---|---|---|---|---|
| 8,827,936 B1* | 9/2014 | Adaie | A61H 9/0078 | 601/121 |
| 9,119,705 B2* | 9/2015 | Parish | A61F 7/0085 | |
| 2003/0070236 A1* | 4/2003 | Barker | A61B 5/00 | 5/658 |
| 2003/0197614 A1 | 10/2003 | Smith et al. | | |
| 2004/0040091 A1* | 3/2004 | Hampe | A61G 7/05 | 5/503.1 |
| 2004/0186358 A1* | 9/2004 | Chernow | A61B 5/0002 | 600/300 |
| 2005/0177342 A1* | 8/2005 | Busch | A61B 6/4441 | 702/183 |
| 2005/0273940 A1* | 12/2005 | Petrosenko | A61B 5/1126 | 5/722 |
| 2008/0094589 A1* | 4/2008 | Panitz | G03B 21/00 | 353/122 |
| 2008/0173784 A1 | 7/2008 | Mason et al. | | |
| 2009/0237264 A1* | 9/2009 | Bobey | A61G 7/05776 | 340/815.69 |
| 2011/0030141 A1* | 2/2011 | Soderberg | A61G 7/015 | 5/600 |
| 2011/0169653 A1* | 7/2011 | Wang | A61G 7/005 | 340/686.6 |
| 2013/0048705 A1* | 2/2013 | Tallent | G06Q 10/06 | 235/375 |
| 2013/0342350 A1* | 12/2013 | Popescu | G08B 21/02 | 340/573.1 |
| 2014/0259410 A1* | 9/2014 | Zerhusen | A61G 7/00 | 5/600 |
| 2014/0276291 A1* | 9/2014 | Mansur, Jr. | A61H 9/0078 | 601/152 |
| 2015/0187196 A1* | 7/2015 | Blair | G16H 40/63 | 340/691.6 |
| 2015/0257952 A1* | 9/2015 | Zerhusen | G08C 17/02 | 340/12.5 |
| 2018/0049932 A1* | 2/2018 | Zerhusen | A61G 12/00 | |

* cited by examiner

STATUS OR ALARM INDICATOR DEVICE

This application is a continuation-in-part of International Application No. PCT/US2016/015860 filed Jan. 30, 2016, pursuant to 35 USC 365(c), which claims priority to U.S. Provisional Patent Application No. 62/110,229 filed Jan. 30, 2015, the disclosures of which are hereby incorporated in their entirety by reference.

TECHNICAL FIELD

The present disclosure relates to a status or alarm indicator device for use in hospital or care facilities, and in particular to a device designed to provide at least one downwardly directed indicator light beam.

BACKGROUND

Some devices used in the hospital or home care environments may have indicators for relaying a status of the device and/or patient. Such devices may include an acoustic transmitter for emitting a warning or alarm signal. In the alternative or in addition, the device may have a visual indicator. A visual indicator can be less disturbing to patients and hospital staff than an acoustic indicator and is especially useful for indicating status and minor alarms. A visual indicator is also optimal during periods of rest, for instance at night, when the indicator remains effective even when ambient lighting has been lowered or switched off.

A difficulty with visual indicators, however, is that they often are only visible when a caregiver/healthcare provider comes within sufficient proximity to read the device's monitor. Additionally, visual indicators can become obscured, for instance when the indicator and/or device is hidden behind other equipment, is covered, for example by bedding drapes, or when the device monitor faces away from caregivers/healthcare providers. When this happens, the indicator can fail to provide its intended function. Accordingly, improvements are desired to address at least the aforementioned shortcomings.

SUMMARY

Embodiments of the present disclosure relate to an improved status or alarm indicator device.

According to an exemplary embodiment of the present disclosure, there is provided an indicator device for indicating a status or condition related to a patient, patient therapy and/or medical device or equipment associated with the patient. The indicator device includes a casing having upper and lower ends; at least one connector capable of being coupled to a support, such that the lower end of the casing is displaced above but faces a downward direction towards a floor; and at least one lighting element disposed to emit light from the lower end of the casing; the lighting element being operable to generate a light indicative of the status or condition and in a downwards direction towards the floor. The emitted light optionally may be in the form of a light beam.

According to another exemplary embodiment of the present disclosure, there is provided an indicator device for indicating a status or condition related to a patient, patient therapy and/or medical device or equipment associated with the patient. The indicator device includes a casing having upper and lower ends. At least one connector of the device is capable of being coupled to a support, such that the lower end of the casing faces an upwards direction towards a ceiling. At least one lighting element is disposed to emit light from the upper end of the casing, the lighting element being operable to generate a light indicative of the status or condition in an upwards direction towards the ceiling. The emitted light optionally may be in the form of a light beam.

The example device illustrated and described herein is able to produce a downwardly directed beam of light which can reflect off, for example, a floor surface to provide a status or warning indicator to a care giver. The device can usefully operate even when covered by a drape or obstructed by other apparatus or devices. Furthermore, the visual indication is unobtrusive to patients.

In an illustrative embodiment, the at least one connector may include a hook element, and in another embodiment may include at least two hook elements. Connectors of this type make it easy to reversibly attach the device to a footboard of a bed or other support structure. At least one connector may be disposed on a rear of the casing.

In an illustrative embodiment, the at least one connector is configurable between a deployed condition and a storage condition. In the storage condition the at least one connector is disposed within a perimeter of the casing. For this purpose, the rear of the casing may include at least one generally flat support surface, which advantageously acts to maintain the casing in a generally vertical orientation when attached to a support and may also allow the casing to be positioned on its back or to lay on its side on a horizontal surface. The casing may include first and second generally flat support surfaces. For these purposes the casing may include at least one projecting member to which at least one connector is attached, the at least one projecting member providing the at least one generally flat support surface.

In an illustrative embodiment, the casing includes a window in its lower end, the at least one lighting element being disposed in the casing and arranged to transmit the emitted light from the front face of the casing through the window. The window may be frosted, which causes the light to spread, allowing reflection off other surfaces such as off a footboard.

In an illustrative embodiment, the casing includes a front face and at least one frontal lighting element disposed to emit light from the front face of the casing; the at least one frontal lighting element being operable to generate a status or warning light. The device may therefore provide a multitude of status or warning lights, which may provide the same status or warning indicators as one another, though not necessarily so.

In an illustrative embodiment, the casing may include at least one frontal window, and at least one frontal lighting element may be disposed in the casing and arranged to emit light from the front face of the casing through the at least one frontal window. Advantageously, the at least one frontal window may be disposed at or adjacent the upper end of the casing, light from the at least one frontal lighting element being directed at least partially in a direction from the upper end of the casing. The at least one frontal window may be disposed at an angle at least partially facing the upper end of the casing.

In an illustrative embodiment, the casing may include first and second frontal windows, disposed at or adjacent opposing edges of the casing. Optionally, the frontal window may be at least partially frosted or completely frosted.

In an illustrative embodiment, the casing may also or in the alternative include at least one upper lighting element disposed to emit light from or adjacent the upper end of the casing. The at least one upper lighting element may be operable to generate, emit and/or transmit a status or warning light. For this purpose, the casing may include at least one upper window, the at least one upper lighting element being disposed in the casing and arranged to generate a light beam through the upper window. Optionally, the at least one upper window may be frosted.

The at least one lighting element may include at least one light or lamp, which may be colored and/or filtered. At least one of, and potentially each light or lamp may be a light emitting diode. In one embodiment, these light(s) or lamp(s) may have sufficient lumens to directly illuminate and reflect light from a surface of the floor and/or ceiling of a standard size hospital room, irrespective of the location of device within the room.

The teachings herein also provide a hospital or home care apparatus including an indicator device as specified herein. The apparatus may be a pump, such as an air pump for a DVT (deep vein thrombosis) cuff or any other medical device. The pump may be configured to monitor and control over a period of time pressure applied to a cuff when a cuff is in fluid communication with the pump. The cuff, which may be configured as a wrap or garment, can be included with the pump, or otherwise reversibly connectable to the pump.

The emitted light for the indicator device or hospital/home care apparatus may be in the form of a beam. The light emitted from the lower end of the casing may be viewable at least primarily as reflected, indirect light. At least a majority of the light emitted from this bottom surface of the casing may be viewable as indirect light, and may be observed as indirect light reflected off of a surface remote from the indicator device. The light may also be observed as indirect light reflected between the surface remote from the indicator device and the lower end of the casing. The remote surface may be a floor surface, including for instance a floor surface constructed in linoleum, PVC or vinyl.

In example embodiments, light emitted from the front face of the casing may be observed as direct light. The status or warning light of the indicator device may also be (i) observable primarily as indirect light when at least the top half of the indicator device is covered or obscured by a covering, and/or (ii) observable primarily as direct light when at least the top half of the indicator device is not obscured or covered by the covering.

The teachings herein may also include a method for operating and/or using the indicator device disclosed herein, as well as a method for monitoring the status of the indicator device. According to an example embodiment, the example method may involve observing emitted light from the indicator device, wherein the emitted light relates to the status or alarm condition, and the emitted light is primarily observed as indirect light when the indicator device is at least partially covered by a cover. The method may further involve adjusting the pump in reaction to the observing step. The observing step may also include observing emitted light from the indicator device as either direct light or indirect light when the indicator device is not at least partially covered by a cover. According to some embodiments, the observing step may include observing emitted light from the indicator device as primarily direct light when the indicator device is not covered by a cover or other object.

In an exemplary embodiment of the disclosure, there is presented a method for using an indicator device indicative of a condition or status relating to a patient, patient therapy and/or medical device or equipment associated with the patient. The method may include emitting light from the indicator device that is indicative of the status or condition. When a portion of the indicator device is at least partially obstructed, the emitted light may be observed as indirect, reflected light. The method may further involve taking responsive action in relation to the patient, patient therapy or medical device or equipment upon observing the indirect, reflected light.

The step of observing the emitted light as indirect, reflected light may involve predominantly observing the emitted light as indirect, reflected light. Additional steps may involve adjusting the position of the indicator device such that the indirect, reflected light is directed towards a remote location, away from the patient. An orientation of a lighting element of the device may be adjusted with respect to the indicator device housing to facilitate observation of the indirect, reflected light.

In one embodiment, the indicator device may be part of a pump configured to regulate pressure to a pressure cuff in fluid communication with the pump, wherein taking responsive action involves adjusting the cuff pressure. In another embodiment, the indicator device may be any one of the devices described in the present disclosure.

Other features and aspects of the disclosure herein will become apparent from the disclosure of the example and illustrative embodiments which follows.

BRIEF DESCRIPTION OF THE DRAWINGS

Embodiments of the present disclosure are described below, by way of example only, with reference to the accompanying drawings, in which.

DETAILED DESCRIPTION OF THE EXEMPLARY EMBODIMENTS

Various embodiments of the teachings herein are described below, by way of example only. The illustrative embodiment is configured as an air pump (i.e., a pneumatic pump) which in practice can be used to control the inflation and deflation of a cuff for the treatment of deep vein thrombosis (DVT). It is to be appreciated, though, that the teachings herein are not restricted to use in such a device. They could be incorporated in other hospital or home care devices and may also be incorporated in a stand-alone indicator device which serves no other purpose than to provide an indication of status or warning from an external device such as, for example, a pump, monitoring equipment, control device such as a bed control and so on. The indicator may be part of or used in association with any patient therapy, patient monitor or hospital or home care equipment for which it would be desirable to have patient, therapy and/or device status indicators, such as: pumps; inflatable mattresses, mattress covers, or patient supports; adjustable or therapeutic hospital beds or chairs; components of a hospital bed such as the brakes and/or side rails of the bed; medical devices and apparatuses for preventing pressure ulcers; medical devices and apparatuses for venous thromboembolism, deep vein thrombosis and/or pulmonary embolism prevention and therapy; patient vital sign monitors; etc. The skilled person will readily be able to incorporate the teachings herein into a variety of different hospital devices and apparatus. The indicator of the device can generally be used to provide a status, warning or alarm condition associated with: (i) a patient (e.g. physiological parameters of a patient, such as pulse rate, blood pressure, body temperature or respiration rate, or an environmental condition of the patient, such as adjacent moisture or humidity levels), (ii) therapy, therapy status being applied or delivered to the patient, or the patient's response to the delivered therapy (e.g. therapy duration, therapy rate, etc.), (iii) the status of the device performing and/or delivering the therapy to the patient (e.g. any detected device failures or defects, disconnection of device components, low or no power warnings, electrical surge or high temperature warnings, other device environmental warnings, device maintenance warnings, etc.), and/or (iii) the status of medical equipment associated with a patient (e.g. status or position of a patient bed or chair). Additionally, interchangeable throughout this disclosure as further variations and alternatives, the illustrative embodiments may provide a status or alarm condition related to any one or combination of the following; (i) a patient, (ii) therapy or therapy status being applied or delivered to a patient, (iii) a DVT cuff wearable by a patient, especially in a hospital or home care setting and/or (iv) a pump in fluid communication with a DVT cuff or otherwise configured to be connected to and establish fluid communication with a DVT cuff.

Figure 1:
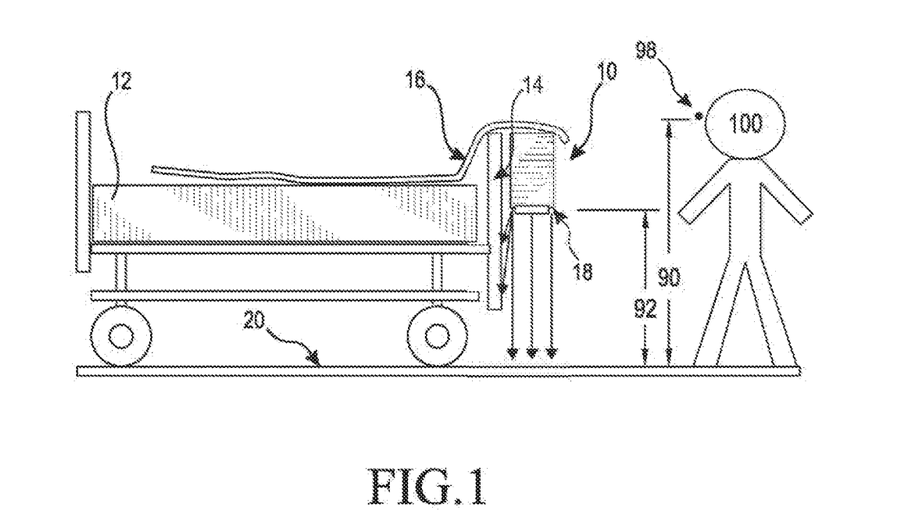
FIG. 1 is a schematic diagram of a hospital bed to which is attached an embodiment of a status or alarm indicator device.

Referring first to FIG. 1, illustrated is a schematic diagram depicting an exemplary embodiment of the indicator device in one mode of use. Specifically, the device 10 is shown attached to a footboard 14 of a patient bed 12. A cover or drape 16 has been placed over the bed 12 and happens to drape over the footboard 14 and device 10, as depicted in the sketch of FIG. 1. The device 10 has an upright configuration, and when hung from the top of or otherwise coupled to the footboard 14 in the upright orientation includes a lower surface or base 18 which faces the floor 20 and is elevated off the floor 20 by a first height 92. As is described in further detail below, the device 10 includes one or more lighting elements, such as lights or lamps, and in the example embodiment the one or more lighting elements are light emitting diodes (LEDs), and may be configured to direct their light downwardly from the device, that is towards the floor 20, especially the portion of the floor 20 that is directly underneath the device 10. In the example shown in FIG. 1, the lighting elements, such as lights or lamps, may also direct light sideways or at an angle, so that at least some of the light directly illuminates a portion of footboard 14, as shown in FIG. 1. In one embodiment, the light or lamp is mounted on a lower and/or side surface of device 10 so as to be oriented downward to directly illuminate at least a portion of the floor. Light striking the ground is reflected upwards and/or outwards, indirectly illuminating at least a disperse portion of the patient's room and/or hallway, thereby more easily attracting the attention of a caregiver. In another embodiment, the light or lamp may be downwardly angled so that it directly illuminates the portion of the floor directly beneath device 10 and/or a portion of the floor distal to and spaced apart from a support surface, such as bed 12, to which device 10 is coupled. By directing light away from a patient bed 12, the indicator may not disturb the patient and/or may be more readily visible to the caregiver/healthcare. The light or lamp may have sufficient lumens to clearly directly illuminate and be reflected from the floor. The lights or lamps of the device 10 may be chosen in their design to provide either (i) a green light, indicating that all is well or (ii) a yellow light acting as a warning, for instance that equipment associated with the device or the patient requires attention. The person skilled in the art will appreciate that other colored lights may be used and that the device 10 may generate more than two lights to indicate a variety of different conditions or statuses of either or both of the apparatus or a patient the apparatus is adapted to relate to. For example, a third red light may be used to indicate a critical failure or endangerment of the patient, delivered patient therapy, medical device delivering therapy to the patient and/or medical equipment associated with the patient. A skilled person will also appreciate that as an alternative or in addition to using colored lights to indicate patient, therapy and/or device status, the same can be accomplished by utilizing different flashing light patterns and/or brightness levels.

The feature of directing light to the floor 20 or footboard 14 results in light being reflected off these surfaces and to be readily visible to a caregiver 100 as indirect light. In practice, the bed 12 may be located behind a privacy curtain or disposed within a room. A caregiver 100 will be able to see from an observation point 98 the visual indications given by the device 10 underneath the curtain or from outside the room, and in a manner which does not disturb a patient (not shown) resting in the bed 12 or other nearby patients. Moreover, the device 10 can continue to provide a visual indication of status or warning even when a cover 16 is draped over the device 10, or if other equipment is located in front of the device 10 obscuring the device 10 itself from the caregiver 100. As shown in FIG. 1, the observation point may be at "eye level" for the caregiver 100, and elevated from the floor at a height 90 which is further elevated than the lower surface or base 18.

Figure 2:
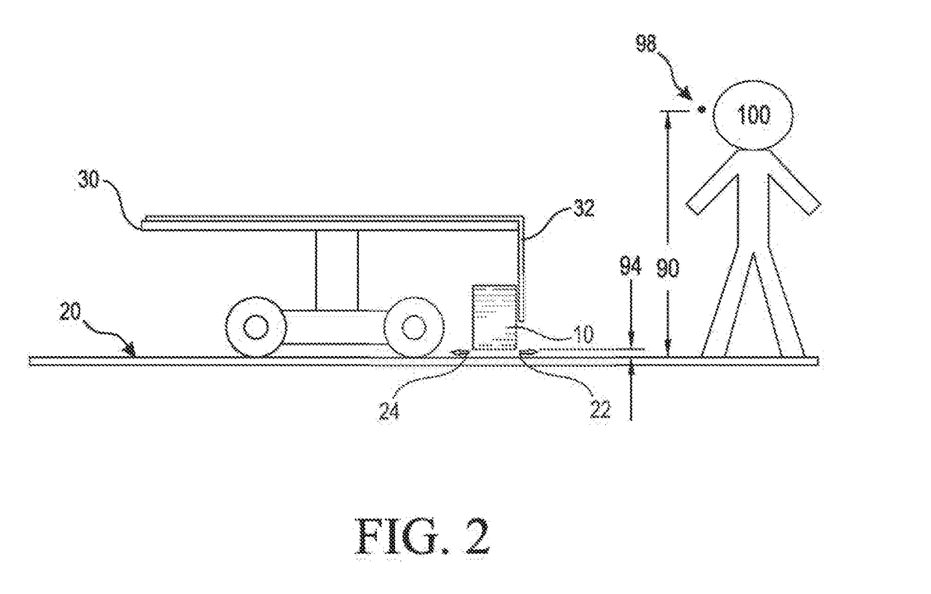
FIG. 2 is a schematic diagram showing another example usage of the status or alarm indicator device as taught herein, more specifically, a status or alarm indicator device shown in proximity to a surgical table.

Referring now to FIG. 2, illustrated is another example of usage of the device 10, in this case positioned beside an operating table 30 and specifically on the floor 20 under the operating table 30. The lights or lamps of the device 10 are arranged such that the emitted light is able to spread along or be bounced/reflected off the floor 20. In one embodiment, the light is reflected at least in a forward direction 22 (wherein forward is generally the direction the controls and/or displays of the device 10 face the user of such controls and displays) and in some embodiments also in a rearward direction 24 (wherein rearward is generally the direction a user addressing the device would face, which is generally opposite the forward direction). The device 10 is, therefore, able to provide a visual indicator status or warning when hooked onto a support such as a hospital bed (and thereby elevated to a height 92 as in FIG. 1) and also when placed at floor level (and thereby not elevated or only elevated a height 94 per FIG. 2 wherein the height 94 is substantially smaller than the height 92). In some embodiments the device 10 may direct light adjacent floor level without relying upon reflection off the floor or another surface. Again, in the example of FIG. 2, there may be a cover, drape or sheet 32 covering the top surface of the operating table 30 and overhanding the top surface in a manner that extends over the device 10. As such, the upper portion and top surface of the front-facing portion of device 10 would not be viewable to the extent the sheet 32 is located intermediate the device 10 and the caregiver 200 addressing the device 10.

Figure 3:
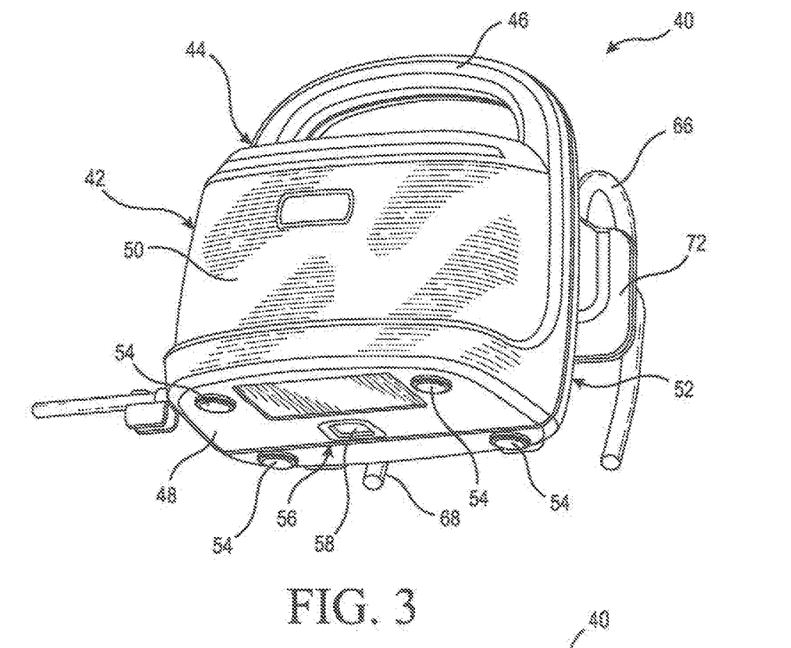
FIG. 3 is a perspective bottom view of an example embodiment of the indicator device.
Figure 4:
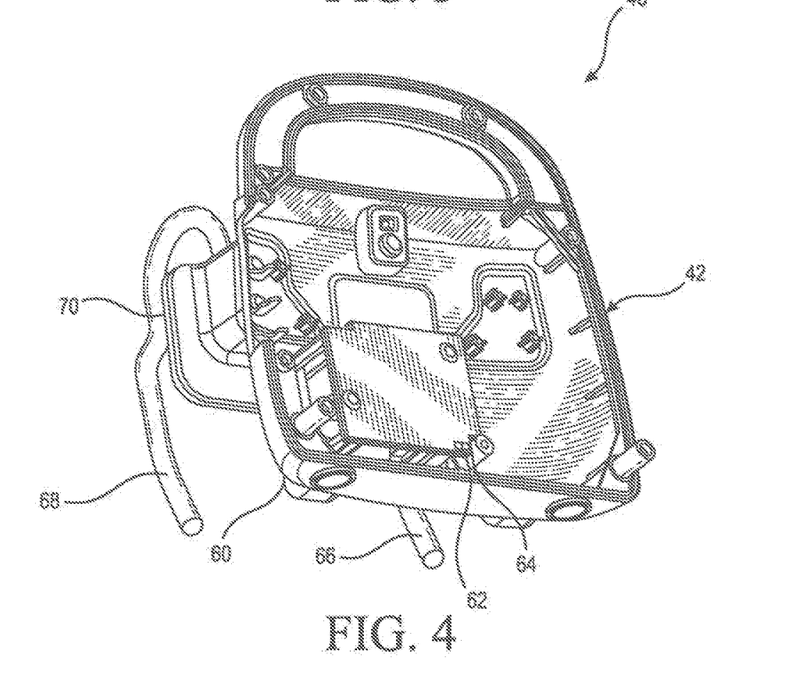
FIG. 4 is a perspective view of the internal components of the example indicator device embodiment of FIG. 3.

Referring now to FIGS. 3 and 4, illustrated are embodiments of a device 40 having the same and/or similar characteristics described above in connection with device 10 of FIGS. 1 and 2. The device 40 may be configured as an air pump for use in pressurising a cuff, such as an ankle cuff, used in the treatment of deep vein thrombosis (DVT). For this purpose, the device 40 will include a pump motor, suitable inlet and outlets for coupling to an inflatable cuff, as well as a control unit provided input/output device for controlling the pump and the resulting pressurization and depressurization of the cuff. These components are common for such air pumps and therefore are not described herein in further detail. As explained above, this is just one example as to how the indicator device taught herein can be implemented in hospital apparatus and the embodiment is, therefore, not limited to the internal components or other functionality of the air pump 40.

The device 40 is shown to include a casing 42 which has an upper region or end 44, and in the example shown is provided with a handle 46 overarching an upper region 44 and spanning opposite sides of device 10. The casing 42 also has a lower end, (e.g., underside) or base 48, which in the embodiment illustrated is shown to be substantially planar and configured to rest on a floor surface 20. The casing 42 also includes a front face 50, a rear side 52, and side portions extending between the front face 50 and rear side 52. The lower end or base 48 is shown provided with a plurality of feet 54, in this case there being four, disposed proximate the edges of the base 48. In the embodiment shown in FIGS. 3 and 4, the feet 54 are relatively short, that is they do not extend beyond the surface of the base 48 by more than a few millimetres. In other embodiments, the feet 54 can be substantially longer, so as in practice to lift the base 48 above the surface of a floor or other support surface (such as by the elevation or height 94 of FIG. 2). The feet 54 may, for example, have a length of a few centimetres, and in other embodiments five or less centimetres.

Base 48 also includes a window 56, which may be positioned close to its centre point and which is enclosed in this embodiment by a panel 58 that may be frosted, translucent, constructed of ABS material, and is not colored or tinted. The frosted panel 58 allows light to pass through it, with the frosting acting to dissipate light, so that in practice to generate a widening beam of light emanating from the base of the device 40 and capable, for example, to reflect off a footboard 18 or other adjacent surface. In other embodiments, the frosted panel 58 could be replaced by a lens.

Referring specifically to FIG. 4, illustrated is the rear portion 60 of the casing 42 when opened or otherwise separated from a removed front portion of the casing 42. Only the relevant components of the device 40 are shown, in particular lighting elements configured as two light emitting diodes 62, 64 which are used to generate the visual indication. These diodes 62, 64 are chosen to generate and emit, respectively, a light of a first color and a light of a second color different than the first color, such as a green light and a yellow light. This allows for the LED 62 to provide for an "all clear" status indication (or first status condition), while the LED 64 provides an alarm or warning indication (or second status condition different than the first status condition). The skilled person will appreciate that the LEDs 62, 64 are an example only of suitable lighting elements and that these may take any other form, including but not limited to incandescent lights or lamps, optical fibres and multi-colored lamps such as multi-colored LEDs. In the case of multi-colored lights or lamps, the two LEDs 62, 64 could be replaced by a single light or lamp unit.

LEDs 62, 64 or other embodiment of the lighting elements, e.g. lights and lamps, of device 10 may be inset and flush with respect to base 48 of the housing or casing 42 of device 10 such that light emanating therefrom is orthogonal to a the lower surface of device 10's housing. In another embodiment, LEDs 62, 64 or other embodiment of the device 10 lights and lamps may also be mounted to a front, back, left or right side surface of device 10 and oriented in a downward oriented, floor facing direction. In another exemplary embodiment, the lighting elements (such as lighting units including LEDs 62, 64 and similar lights or lamps of window 74, 76 described below) may be adjustably mounted with respect to the housing or casing 42 such that a user may be able to movably orient and position the lights or lamps of device 10 and the resulting direction of its emitted light. In such an embodiment, a user may be able to adjust the angle, pivot and/or rotate the lights or lamps so as to redirect the light to the closest reflective surface or otherwise orient the light to optimize reflection towards the caregivers and/or away from a patient.

Disposed within the casing 42 there will also be provided driving electronics for powering the LEDs 62, 64 and, as appropriate, monitoring and/or control elements for monitoring the status of the pump or an external device or probe, as well as for driving the LEDs 62, 64 to generate the appropriate illuminating indication. These components will be readily familiar to a person skilled in the art and therefore are not described or shown for the sake of clarity of the description of the teachings herein.

The device 40 also is illustrated to include, in this example, first and second connectors or connecting members 66, 68, which are in the form of generally inverted U-shaped or J-shaped hooks. The hooks 66, 68 include one end which fits into or is otherwise connected to a part of the casing 42, described in further detail below, and may have their other ends free so as to hook over a support, such as a footboard 14 of a hospital or home care bed. The hooks 66, 68 are sized so as to have a sufficient distance between the two prongs of the U-shape so as to fit either side of a footboard 14 and in the embodiments shown have a kink in the free prong which in practice provides two widths to the U-shape to accommodate headboards of different thicknesses.

The casing 42 also includes two rearwardly projecting elements 70, 72, visible better in later drawings and described further below, to which the hooks 66, 68 are attached and from which they extend. The projecting elements 70, 72 have rearwardly facing surfaces which will in practice rest against a footboard 14 in a manner as to hold the casing 42 against the footboard 14 with the lower end or base 48 substantially perpendicular to the footboard 14 and in practice substantially parallel to a floor surface 20. Thus, in such an "upright" orientation, light emanating from the LEDs 62, 64 through the panel 58 of the window 56 will be directed downwardly towards the floor.

Figure 5:
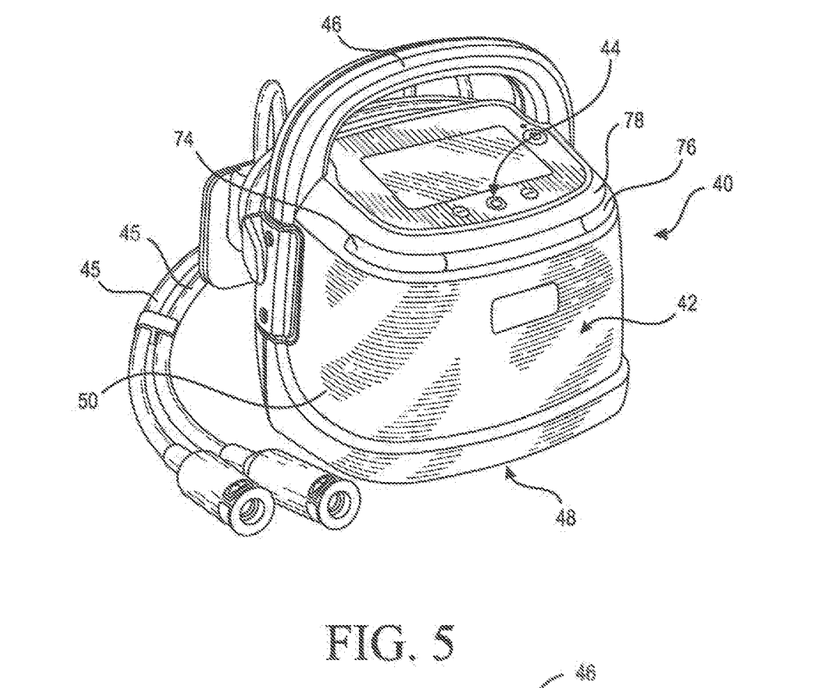
FIG. 5 is a front perspective view of the example indicator device embodiment of FIG. 3.
Figure 6:
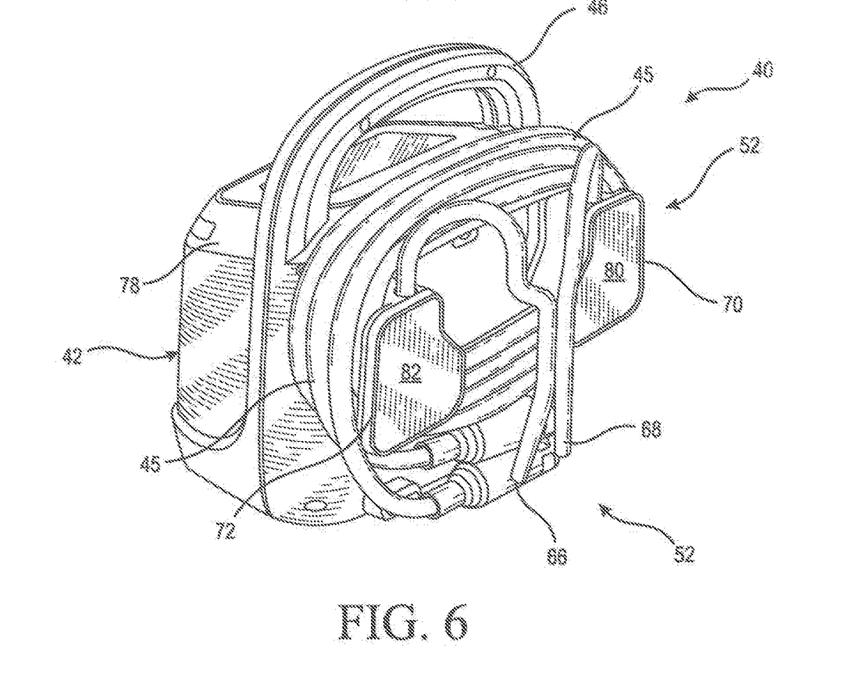
FIG. 6 is a rear perspective view of the example indicator device embodiment of FIG. 3.
Figure 7:
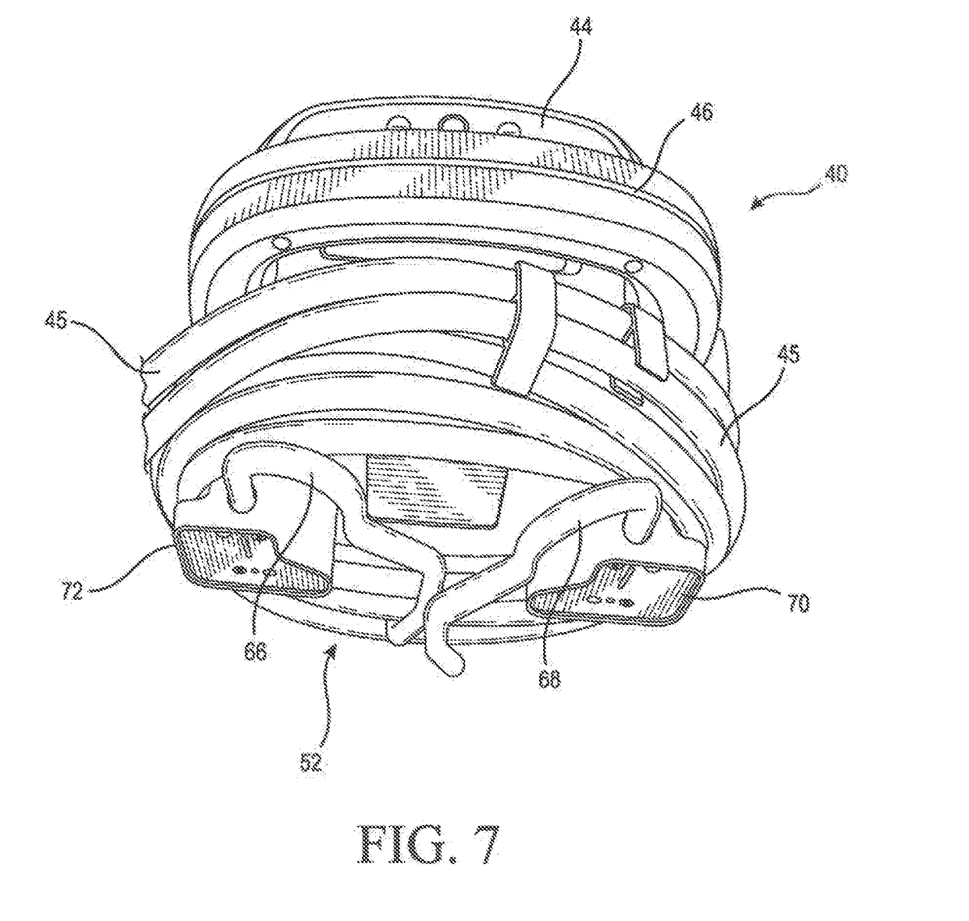
FIG. 7 is a top perspective view of the example indicator device embodiment of FIG. 3.

Referring now to FIGS. 5 to 7, illustrated in better detail are views of the example embodiment of indicator device 40 incorporated into an air pump, including for instance an air pump configured to be used with a DVT cuff. The device 40 includes air tubes 45 for the pump of the system, which do not form part of the indicator device save for the fact that the device 40 will monitor and/or manage the pressure of air within the tubes 45, in practice within a cuff attached to the tubes 45, and provide a visual indication of its status, either alone or in combination with audible indication of its status.

As can be seen in particular within FIG. 5, the device 40 also includes upper window elements 74, 76, which again are enclosed within the casing 42 by frosted clear ABS plastics panels which wrap around the upper edges of the casing 42. The device 40 includes additional lighting elements equivalents to LEDs 62 and 64, to generate light beams through the windows 74 and 76. As can be appreciated particularly from FIGS. 5 and 6, the casing 42 includes a sloping section 78 between its front surface 50 and its upper surface 44, which is disposed at an angle both to the horizontal and to the vertical, for instance at an angle of around 45°. The windows 74, 76 are disposed in this section 78 and therefore face both forwardly and upwardly. Moreover, the wrap-around form of the windows 74, 76 results in the windows also wrapping around the side edges and front of the casing 42, in such a manner that light emanating from the windows 74, 76 will extend both forwardly, upwardly and to either side of the casing 42 and device 40 so as to be visible as direct light from the windows 74, 76. In one embodiment, the light emanating from windows 74, 76 may directly illuminate at least a portion of the ceiling and/or mid to upper region of the walls; a portion of the ceiling directly above device 10; or a portion of the ceiling or walls distal to and spaced apart from the bed. Light striking the ceiling is reflected downwards, indirectly illuminating at least a disperse portion of the patient's room and/or hallway, thereby more easily attracting the attention of a caregiver. Light striking the walls may be similarly reflected throughout the room. In another embodiment, the light or lamp may be upwardly angled so that it directly illuminates the portion of the ceiling directly above device 10 and/or a portion of the ceiling or walls distal to and spaced apart from a support surface, such as bed 12, to which device 10 is coupled. By directing light away from a patient bed 12, the indicator may not disturb the patient and/or may be more readily visible to the caregiver/healthcare. When combined with a window 56 in the base 48, the device 40 can therefore emit light in a multitude of directions, so light emitted may be viewed as either direct light and/or as indirect light originating from the device 40. This can be achieved by illuminating all of the lights or lamps of one color simultaneously or, as appropriate, illuminating only one or more of each type of light or lamp during a status or warning indication.

As can be seen in particular from FIG. 6, the projecting elements 70, 72 at the rear 52 of the casing 42 have substantially flat and co-planar surfaces 80, 82 which may be substantially perpendicular to the base 48. The projecting elements 70, 72 also are shown to have, in this embodiment, narrower "necks" connecting to the rear wall of the casing 42, so as to provide recesses for holding the tubes 45 of the pump, and further provides for the tubes to be wrapped around the projecting elements in a repeated manner as can be seen in FIGS. 5 to 7.

The connecting members or hooks 66, 68 are secured within appropriate recesses or bores in the projecting elements 70, 72 and are able to swivel with respect to the elements 70, 72 so as to extend perpendicularly outwardly in the deployed configuration, as can be seen in FIGS. 3 and 4. Said differently, a plane bisecting hook 68 may be substantially parallel to a plane bisecting hook 66. They can also be swung inwardly, and in one embodiment may be swung inwardly enough so that their free ends fit within the gap between the two projecting elements 70, 72 as will be apparent in particular from FIG. 7. In an exemplary embodiment, the hooks are able to rotate beyond the plane of the co-planar surfaces 80, 82, such that when the hooks 66, 68 are so stored, the outermost perimeter of the casing 42 at its rear is provided by the flat surfaces 80, 82 of the projecting elements 70, 72.

The hooks 66, 68 may press against one another when in the storage condition, so as to hold one another in position by spring force.

The flat surfaces 80, 82 of the projecting elements 70, 72 will abut against a foot board 14 or other vertical support element and support the device 40, that is the casing 42, in a substantially upright orientation, similar to the upright orientation shown for example in FIGS. 5 and 6. Thus, the base 48 will be kept substantially horizontal and generally parallel to the floor surface 20.

The device 40 can be placed on a floor 20 in a manner depicted in FIG. 5. Feet 54 may be of sufficient height and/or the lower surface of device 40 may be angled so as to taper/flare from a central region towards the lower surface edges of device 40 to reflect light outward from beneath device 40. In other embodiments when feet 54 are relatively short, the lower window 56 may be at least partially, and sometimes completely obscured by the floor 20, but the device 40 will still provide the necessary status and/or warning indications by virtue of light emitted from the windows 74, 76. This light will be substantially at floor level so as to avoid any overhanging drape 16 or 32 and can generate light which extends not only around floor level but also upwardly, so as to be readily visible to the caregiver. The light or lamp may have sufficient lumens to clearly directly illuminate and be reflected from a standard size hospital room ceiling and/or walls. The configuration of the device 40 shown in FIG. 5 in particular is particularly useful when short feet are used. Where longer feet 54 are provided to space the base 48 from the floor surface 20, light emanating from the window 56 is able to spread sideways and bounce off the floor so as to be visible to a caregiver. This could also be achieved by standing the device 40 on a raised support. In embodiments with a raised base 48 brought about by longer feet, for instance, the windows 74, 76 and associated lights or lamps could be omitted.

The shape of the device 40 casing 42 shown in the Figures also enables it to be placed on its back on the floor. Specifically, once the hooks 66, 68 are in their storage condition, the rear surfaces 80, 82 of the projecting elements 70, 72 can act as feet allowing the device 40 to be placed on what could be called its back, with the feet resting on the floor 20, In this position, the base 48 will be perpendicular to the floor 20 and thus the window 56 will be exposed and able to direct light generally parallel to the floor 20. The windows 74 and 76, when provided, will also be able to direct light substantially at floor level. The device 40 can therefore be positioned in a manner to generate light beams as depicted in FIG. 2, underneath an operating table or patient bed.

When all of the windows 56, 74, 76 and associated lights or lamps are provided and used, the device 40 is able to generate a status or warning light and a multitude of orientations of the device 40, that is when hooked on a bed or other support and also when placed on the floor, be it on the feet 54 as depicted in the configuration of FIG. 5 or when placed on its side as described above.

The person skilled in the art will appreciate that it is not necessary to have three sets of lights or lamps and windows. For example, a single upper window could be provided instead of the two windows 74, 76.

As explained above, although the device 40 is described as an air pump in one embodiment, the status and indication components of the device 40 can be used in other devices, be it medical equipment or in a stand-alone indicator device which can be coupled to a separate monitoring or control device, such as a separate pump system, diagnostic equipment, bed control apparatus and so on.

In an exemplary embodiment, any of the aforementioned indicator devices 10, 40 may be used to facilitate the monitoring, regulation and/or therapeutic treatment of a patient. The device may also be used to monitor a status or condition of a patient therapy and a medical device or equipment delivering therapy to and/or operatively associated with a patient. A caregiver and/or healthcare provider may, for example, be able to quickly assess and/or assess from a distance whether there exists any detected condition of a patient and/or of a medical device or equipment that requires technical and/or medical assessment, attention and/or intervention by observing the light emanating from the indicator device and/or by observing the indirect light reflected from the floor, ceiling, wall or other surface of/in a patient's room and/or adjacent to the indicator device. In one embodiment, the light may be easily observed by glancing into a patient's room without the need to be located sufficiently proximate to the indicator device to read its monitor. In another embodiment, the light may be reflected from a surface of (e.g. floor or ceiling) and/or in the patient's room such that the light is directed into the hallway towards a monitoring caregiver/healthcare provider and away from the patient. In one embodiment, the indicator device may be facing away from a caregiver and/or may be at least partially obstructed by other equipment in the room and/or by items covering a portion of the device and/or indicator, such as bed covering; nevertheless, the light emitted from the indicator is visible as indirect, reflected light observable by and/or directed towards a caregiver/healthcare provider.

In an embodiment of the indicator device 10, 40 in which the lighting elements may be adjustably mounted with respect to the housing or casing 42, a user may movably orient and position the lighting elements so that the emitted light is downwardly focused, directed to the closest reflective surface and/or oriented to optimize reflection towards the caregivers and/or away from the patient. In adjusting the lighting elements, a user may be able to pivotally, angularly and/or rotatably orient the lighting elements to optimize visibility.

The specific color of the light, brightness of the light, projected symbol and/or flashing pattern of the light may be used to convey specific patient, patient therapy and/or medical device or equipment status information to the caregiver and/or healthcare provider. For example, projection of a green color light may convey that no fault in a medical device or equipment operatively associated with the indicator has been detected and/or no monitored physiological parameter of the patient (e.g. pulse, blood pressure, body temperature, respiration rate, etc.) exceeds the normal/standard range. Projection of a yellow light, by contract may convey a warning that: a medical device or equipment fault has been detected (such as a hardware or software fault or defect); the medical device or equipment requires hardware and/or software servicing; standard hardware and/or software maintenance and/or update is due; detection of a potentially dangerous condition of the medical device or equipment, such as high temperatures, electrical surge, low power, disconnection of a medical device or equipment component, or unlocked or locked state of a medical device or equipment component; a monitored physiological parameter of the patient (e.g. pulse, blood pressure, body temperature, respiration rate, etc.) exceeds normal/standard range; and/or a potentially dangerous or undesirable environmental condition affecting a patient exists (e.g. detection of moisture or high humidity adjacent to a patient). When the indicator device is either operatively associated with or a component of a pump medical device, a yellow warning light may indicate a low fluid pressure, fluid leak and/or a kinked or otherwise blocked tubing has been detected. In the instance where the medical device is an air pump operatively associated with a therapeutic pressure cuff (which may be configured as a wrap or garment) for preventing and/or treating DVT, a yellow light may be an indicator of low pressure in the cuff, detection of an air leak in the cuff and/or a disconnection between the cuff and pump. In instances where the medical equipment is a bed, the yellow warning light may indicate the brakes or side rails of the bed are in either an unlocked or locked state. In one embodiment, the indicator device may project light in the form of a specific symbol, such as an image, sign, number, letter or shape, indicative of patient, patient therapy and/or medical device or equipment status information. For example, the projected light may form a flashing, red X or stop sign on the floor, wall or other environmental surface when a fault is detected in the medical device or equipment operatively associated with the indicator device or a green plus sign may be clearly projected from the indicator device and onto a surface when the monitored physiological parameters of a patient (e.g. pulse, blood pressure, body temperature, respiration rate, etc.) are within normal/standard range. In an exemplary embodiment, the indicator device may be a pump, wherein a light source disposed on a lower surface of the pump clearly projects multiple signs, images and pictures indicative of warnings or dangerous situations (e.g. notice of a disconnected pressure garment or detected low pressure of the garment, device error or failure, abnormal patient physiological parameters, etc.) and/or pump operation/therapy status (e.g. pump is turned on, pump is in operation; compression therapy is being administered; and DVT compression therapy cycle is completed, etc.). These signs, images and pictures may be projected from the pump onto a floor or wall adjacent to a patient's bed. Multiple symbols can be projected adjacent to one another to simultaneously provide a caregiver with information regarding a patient's physical status, the operational condition of the pump and/or the progress of a patient's DVT prevention therapy.

In response to the observed direct light or indirect light reflected from a surface in/of the patient room, the caregiver/healthcare provider may respond by reviewing the details of the medical device or equipment warnings, stop the delivery of the therapy performed by the medical device or equipment, or adjust or stop the medical device/equipment or a function thereof. For example, the method may involve adjusting the pump pressure in reaction to the observing step. In the instance where the medical device is an air pump associated with a DVT cuff, the caregiver/healthcare provider may review the details of the warning generated by the medical device and/or adjust the pump, namely adjust the inflation rate, stop air flow and/or deflate the DVT cuff.

While embodiments disclosed may relate to light observable by a caregiver, also disclosed and contemplated are non-human observers such as a light detector which can in all instances replace and/or supplement the observation achieved by the caregiver at certain observation point(s) also achieved by a caregiver, including for instance a caregiver in a standing upright position.

All optional and example features and modifications of the described embodiments and dependent claims are usable in all aspects of the embodiments taught and described herein. Furthermore, the individual features of the dependent claims, as well as all optional and described features and modifications of the described embodiments are combinable and interchangeable with one another.

The foregoing description has been presented for the purpose of illustration and description only and is not to be construed as limiting the scope of the invention in any way. The scope of the invention is to be determined from the claims appended hereto. While various devices and apparatus have been described with reference to certain embodiments within this disclosure, one of ordinary skill in the art will recognize that additions, deletions, substitutions and improvements can be made while remaining within the scope of the invention as defined by the appended claims.

The following abstract is incorporated in the specification: An indicator device (40) includes a casing (42) having rearwardly projecting elements (70, 72) from which coupling hooks (66, 68) extend. The device (40) includes a downwardly facing window (56) as well as two forwardly and/or upwardly extending windows (74, 76). The device (40) includes lights or lamps (62) disposed adjacent the windows (56, 74, 76) for generating status and/or warning signals, typically green and yellow light. The device (40) can be hooked onto a support such as a footboard (14) of a hospital bed (12) or placed on a floor (20) and in all cases has a window (56, 74, 76) which is exposed. The lowermost window (56) at least is able to direct light from the lighting elements (62, 64) to a surface such as a floor (20) or footboard (14) or other surface. This assists in a caregiver seeing light emanating from the device (40) even when this is covered, for example by a drape (16, 32) or other equipment.

The invention claimed is:

1. An indicator device for indicating a status or condition related to a patient, patient therapy and/or medical device or equipment associated with the patient, the indicator device comprising:
    a casing comprising upper and lower ends;
    at least one connector capable of being coupled to a support, such that the lower end of the casing is displaced above but faces in a downward direction towards a floor and the upper end of the casing facing an upwards direction towards a ceiling; and
    at least one lighting element disposed to emit light from the lower end of the casing and projecting downward towards the floor or at least one lighting element disposed to emit light from the upper end of the casing and projecting upward towards the ceiling, the lighting element being operable to generate a light indicative of the status or condition,
    wherein the casing includes a rear face and a front face opposite the rear face, wherein the rear face of the casing includes at least one rearwardly projecting element, wherein the at least one connector includes at least one hook, wherein the at least one hook is attached to and extends from the at least one rearwardly projecting element, wherein the at least one rearwardly projecting element includes a rearwardly facing surface configured to rest against a footboard such that casing is held against the footboard with the lower end of the casing substantially perpendicular to the footboard and substantially parallel to the floor.

2. The indicator device according to claim 1, wherein the at least one hook is configurable between a deployed condition and a storage condition, in which the at least one hook is disposed within a perimeter of the casing.

3. The indicator device according to claim 1, wherein the at least one rearwardly facing surface includes at least one generally flat support surface permitting the casing to lay on its side on a horizontal surface.

4. The indicator device according to claim 1, wherein the casing includes a window in its lower end, the at least one lighting element being disposed in the casing and arranged to transmit the emitted light through the window and wherein the indicator device is configured to project light through the window and onto a surface to form a symbol indicative of the status or condition.

5. The indicator device according to claim 1, wherein the casing includes at least one frontal lighting element disposed at or adjacent the upper end of the casing to emit light from the front face of the casing and at least partially in a direction from the upper end of the casing; the at least one frontal lighting element being operable to generate a status or warning light.

6. The indicator device according to claim 5, wherein the at least one frontal window is disposed at an angle at least partially facing the upper end of the casing.

7. The indicator device according to claim 1, wherein the at least one lighting element includes at least one lamp having a color or a filter.

8. The indicator device according to claim 7, wherein the at least one lamp is a light emitting diode.

9. The indicator device according to claim 1, further comprising:
    the medical device or equipment associated with the patient.

10. The indicator device according to claim 9, wherein the medical device or equipment includes a pump and is configured to monitor and control over a period of time pressure applied to a cuff when the cuff is in fluid communication with the pump.

11. The indicator device according to claim 10, further comprising the cuff.

12. The indicator device according to claim 1, wherein the light emitted is in the form of a beam, such that light emitted from the lower end of the casing is viewable at least primarily as indirect light reflected off of a surface remote from the indicator device.

13. The indicator device according to claim 12, wherein the surface remote from the indicator device is a surface of the floor.

14. An indicator device according to claim 5, wherein the light emitted from the front face of the casing is observed as direct light.

* * * * *